United States Patent
Peticca et al.

(10) Patent No.: US 9,827,364 B2
(45) Date of Patent: Nov. 28, 2017

(54) FILTERS WITH GRADIENT POROSITIES

(71) Applicant: Terumo Cardiovascular Systems, Inc., Ann Arbor, MI (US)

(72) Inventors: Louis F. Peticca, Elkton, MD (US); Jeffrey E. Troyan, Elkton, MD (US); Eric E. Brooking, Bear, DE (US)

(73) Assignee: Terumo Cardiovascular Systems, Inc., Ann Arbor, MI (US)

( * ) Notice: Subject to any disclaimer, the term of this patent is extended or adjusted under 35 U.S.C. 154(b) by 225 days.

(21) Appl. No.: 14/728,241

(22) Filed: Jun. 2, 2015

(65) Prior Publication Data
US 2016/0354530 A1 Dec. 8, 2016

(51) Int. Cl.
*A61M 1/36* (2006.01)
*B01D 19/00* (2006.01)
*B01D 35/30* (2006.01)

(52) U.S. Cl.
CPC ........ *A61M 1/3627* (2013.01); *A61M 1/3632* (2014.02); *B01D 19/0031* (2013.01); *B01D 35/30* (2013.01); *A61M 1/3633* (2013.01); *A61M 2205/75* (2013.01)

(58) Field of Classification Search
CPC .... A61M 1/34; A61M 1/3627; A61M 1/3632; A61M 1/3633; A61M 1/3635; B01D 19/0031; B01D 35/30
See application file for complete search history.

(56) References Cited

U.S. PATENT DOCUMENTS

| 4,303,530 A | 12/1981 | Shah et al. | |
|---|---|---|---|
| 5,770,073 A * | 6/1998 | Bach | A61M 1/3627 210/436 |
| 8,597,417 B2 | 12/2013 | Kobayashi et al. | |
| 8,617,200 B2 | 12/2013 | McIntosh et al. | |
| 2004/0007540 A1* | 1/2004 | Verpoort | A61M 1/0209 210/767 |
| 2013/0197664 A1* | 8/2013 | Ballard | D04H 1/728 623/23.72 |
| 2014/0030149 A1 | 1/2014 | Takeuchi | |

OTHER PUBLICATIONS

International Search Report and Written Opinion dated in corresponding International Application No. PCT/US2016/035204 dated Aug. 22, 2016 (13 pages).

* cited by examiner

*Primary Examiner* — Robert Clemente
(74) *Attorney, Agent, or Firm* — Fish & Richardson P.C.

(57) ABSTRACT

Multiple embodiments of medical filters are described. For example, this document describes extracorporeal blood filters that have a gradient of filter pore sizes at different portions of the filter element. The gradient of filter pore sizes may enhance the filter's potential for capturing and removing gaseous bubbles that may be present in the blood or other fluid that is flowing through the filter.

19 Claims, 3 Drawing Sheets

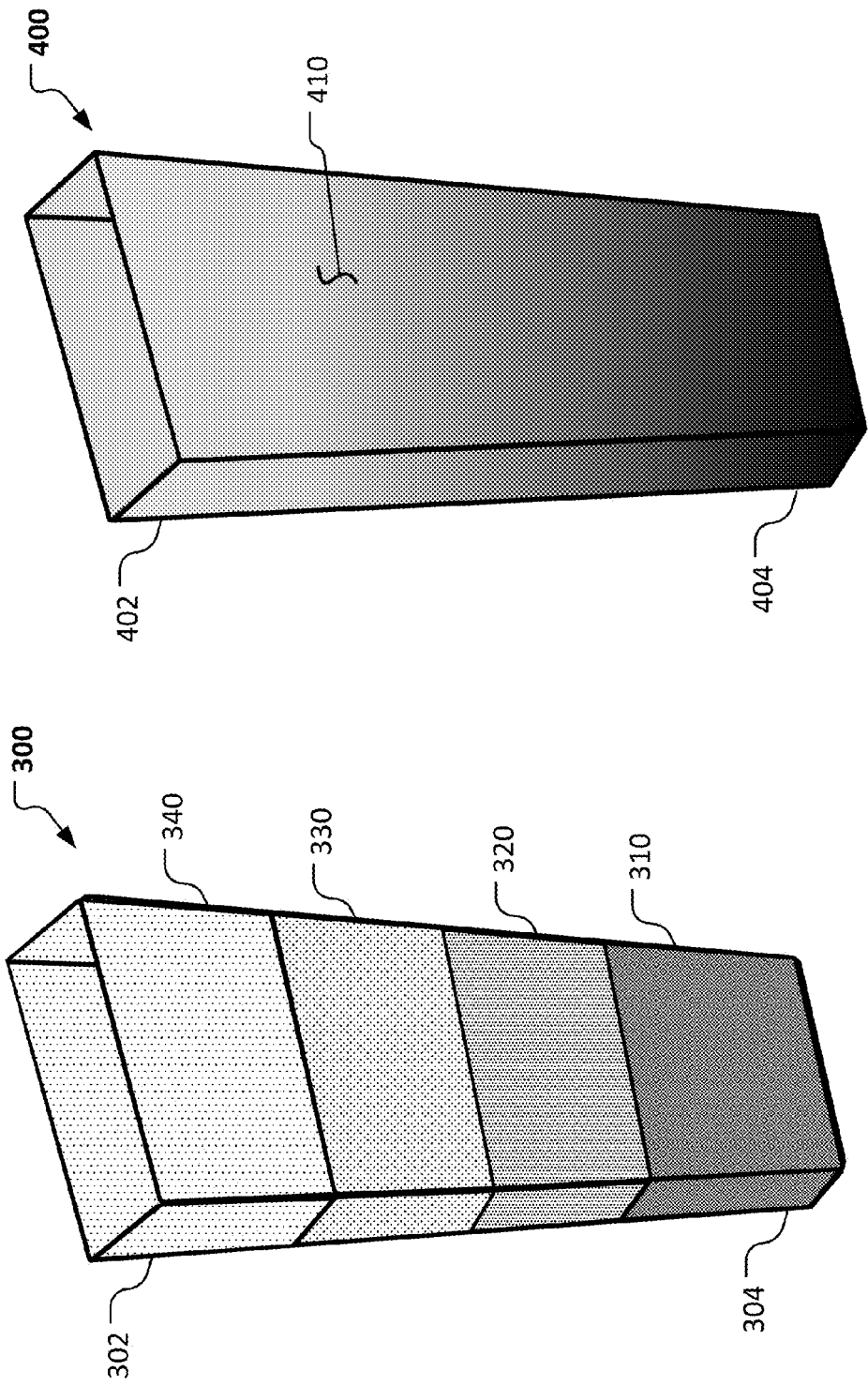

FILTERS WITH GRADIENT POROSITIES

BACKGROUND

1. Technical Field

This document relates to filters. For example, this document relates to filters that have a gradient of filter pore sizes at different portions of the filters. The filters provided herein can be used in medical applications and non-medical applications.

2. Background Information

Fluid systems are often used in a medical context. Some examples of fluid systems used in the medical context include respiratory systems, anesthesia systems, infusion pump systems, blood transfusion circuits, kidney dialysis systems, extracorporeal membrane oxygenation (ECMO) systems, extracorporeal circuits for heart/lung bypass, and the like.

Some such medical fluid systems include the use of filters. For example, in some cases filters are used to remove undesired elements present in the blood that is flowing through an extracorporeal circuit. Such undesired elements within the blood may include contaminants such as clotted blood components and gaseous bubbles.

Gaseous bubbles within the blood of an extracorporeal circuit presents a concern in relation to patient safety. If gaseous bubbles within blood flowing within an extracorporeal circuit make their way to within the circulatory system of the patient, the gaseous bubbles can become emboli that cause the patient to experience a stroke, for example.

In the context of an extracorporeal blood circuit used during open-heart surgery, for example, gaseous emboli may sometimes be introduced into the circuit at the point of cannulation. That is, if the seal between the venous cannula of the extracorporeal circuit and the patient's anatomy is not essentially airtight, air may pass into, or to even be drawn into, the circuit. When that happens, filters within the extracorporeal circuit play an important role in preventing the gaseous bubbles from being delivered to the patient's vasculature and becoming emboli.

SUMMARY

This document provides improvements to filters. For example, this document provides filters that have a gradient of filter pore sizes at different portions of the filters. The filters provided herein can be used in medical applications and non-medical applications. For example, this document provides example extracorporeal blood filters that have a gradient of filter pore sizes at different portions of the filter element. As described further below, the gradient of filter pore sizes may enhance the filter's potential for capturing gaseous bubbles (potential emboli) that may be present in the blood or other fluid that is flowing through the filter.

It should be understood that, in the context of this disclosure, "pore size" refers to an average pore size of filter media or of a particular portion of filter media. Further, it should be understood that the term "adjacent" does not require direct contact between two or more objects (or portions of objects) that are described as being adjacent to each other.

In one implementation, a venous blood reservoir for use in an extracorporeal circuit includes an outer housing defining an internal space, a cardiotomy filter, and a venous filter comprising a porous filter material disposed within the internal space. The outer housing has an upper housing portion and a lower housing portion. The filter has an upper filter end portion and a lower filter end portion. The upper filter end portion is disposed adjacent the upper housing portion and the lower filter end portion disposed adjacent the lower housing portion. An average pore size of the porous filter material disposed at the lower filter end portion is less than an average pore size of the porous filter material disposed at the upper filter end portion.

Such a venous blood reservoir may optionally include one or more of the following features. The venous filter may comprise three or more distinct portions of the porous filter material. The venous filter may also include a middle filter portion. An average pore size of the porous filter material disposed at the middle filter portion may be larger than the average pore size of the porous filter material disposed at the lower filter end portion. The average pore size of the porous filter material disposed at the middle filter portion may be less than the average pore size of the porous filter material disposed at the upper filter end portion. The venous filter may comprise a bag filter. The venous filter may comprise a continuous piece of the porous filter material that has a gradually changing pore size along a length of the filter. The venous filter may comprise four or more distinct portions of the porous filter material. The average pore size of the porous filter material disposed at the lower filter end portion may be less than 40 microns. The average pore size of the porous filter material disposed at the upper filter end portion may be greater than 40 microns.

In another implementation, a method of using an extracorporeal circuit during a surgery on a patient includes transferring blood from the patient into a venous blood reservoir, and draining the blood out of the venous blood reservoir. The venous blood reservoir includes an outer housing defining an internal space, and a venous filter. The venous filter includes a porous filter material disposed within the internal space. The outer housing has an upper housing portion and a lower housing portion. The filter has an upper filter end portion and a lower filter end portion. The upper filter end portion is disposed adjacent the upper housing portion, and the lower filter end portion is disposed adjacent the lower housing portion. An average pore size of the porous filter material disposed at the lower filter end portion is unequal to an average pore size of the porous filter material disposed at the upper filter end portion.

Such a method of using an extracorporeal circuit during a surgery on a patient may optionally include one or more of the following features. The method may further include passing the blood through the venous filter. The average pore size of the porous filter material disposed at the lower filter end portion may be less than the average pore size of the porous filter material disposed at the upper filter end portion. At least some gaseous bubbles may be removed from the blood by the venous filter as the blood passes through the filter. At least some gaseous bubbles may be broken into smaller gaseous bubbles by the venous filter as the blood passes through the filter. The average pore size of the porous filter material disposed at the lower filter end portion may be less than 40 microns, and the average pore size of the porous filter material disposed at the upper filter end portion may be greater than 40 microns.

In another implementation, a medical filter includes a housing defining an internal space, and a filter element comprising a porous filter material disposed within the internal space. The housing has an upper housing portion and a lower housing portion. The filter element has an upper filter end portion and a lower filter end portion. The upper filter end portion is disposed adjacent the upper housing portion and the lower filter end portion disposed adjacent the lower housing portion. An average pore size of the porous filter material disposed at the lower filter end portion is less (finer) than an average pore size of the porous filter material disposed at the upper filter end portion.

Such a medical filter may optionally include one or more of the following features. The filter element may comprise three or more distinct portions of the porous filter material. The filter element may also have a middle filter portion. An average pore size of the porous filter material disposed at the middle filter portion may be larger (coarser) than the average pore size of the porous filter material disposed at the lower filter end portion. The average pore size of the porous filter material disposed at the middle filter portion may be less (finer) than the average pore size of the porous filter material disposed at the upper filter end portion. The filter element may comprise two or more distinct portions of the porous filter material. The filter element may comprise a continuous piece of the porous filter material that has a gradually changing pore size along a length of the filter element. The filter element may comprise four or more distinct portions of the porous filter material.

In another implementation, a method of filtering blood through a filtering system includes inputting the blood to the filtering system at a bottom region of a chamber defined by a filter and an upper air space, and filtering the blood such that the blood flows outwardly through pores in the filter while gaseous bubbles prevented from flowing through the pores in the filter rise in the chamber toward the upper air space. The filter includes a porous filter material. The filter has an upper end portion and a lower end portion. An average pore size of the porous filter material disposed at the lower end portion is less than an average pore size of the porous filter material disposed at the upper end portion.

Such a method of filtering blood through a filtering system may optionally include one or more of the following features. In some embodiments, the average pore size of the porous filter material disposed at the lower end portion is less than 40 microns. In some embodiments, the average pore size of the porous filter material disposed at the upper end portion is greater than 40 microns.

Particular embodiments of the subject matter described in this document can be implemented to realize one or more of the following advantages. In some embodiments, the medical filters provided herein will improve the efficacy of gaseous bubbles removal from the liquid being filtered. Such an improvement may result, for example, because the filters include a gradient of filter pore sizes at different portions of the filter element. Accordingly, the liquid being filtered may incur a longer residence time in the filter housing such that gaseous bubbles have more opportunity to naturally rise and exit from the liquid. Such improved devices and methods may enhance the overall medical procedure efficacy, improve patient safety, enhance patient recovery times, reduce procedure complications, and reduce healthcare costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 3 is an example medical fluid filter having gradient pore sizes at different discrete portions of the filter element, in accordance with some embodiments provided herein.

FIG. 4 is another example medical fluid filter having gradient pore sizes at different portions of the filter element, in accordance with some embodiments provided herein.

Like reference numbers represent corresponding parts throughout.

DETAILED DESCRIPTION

Figure 1:
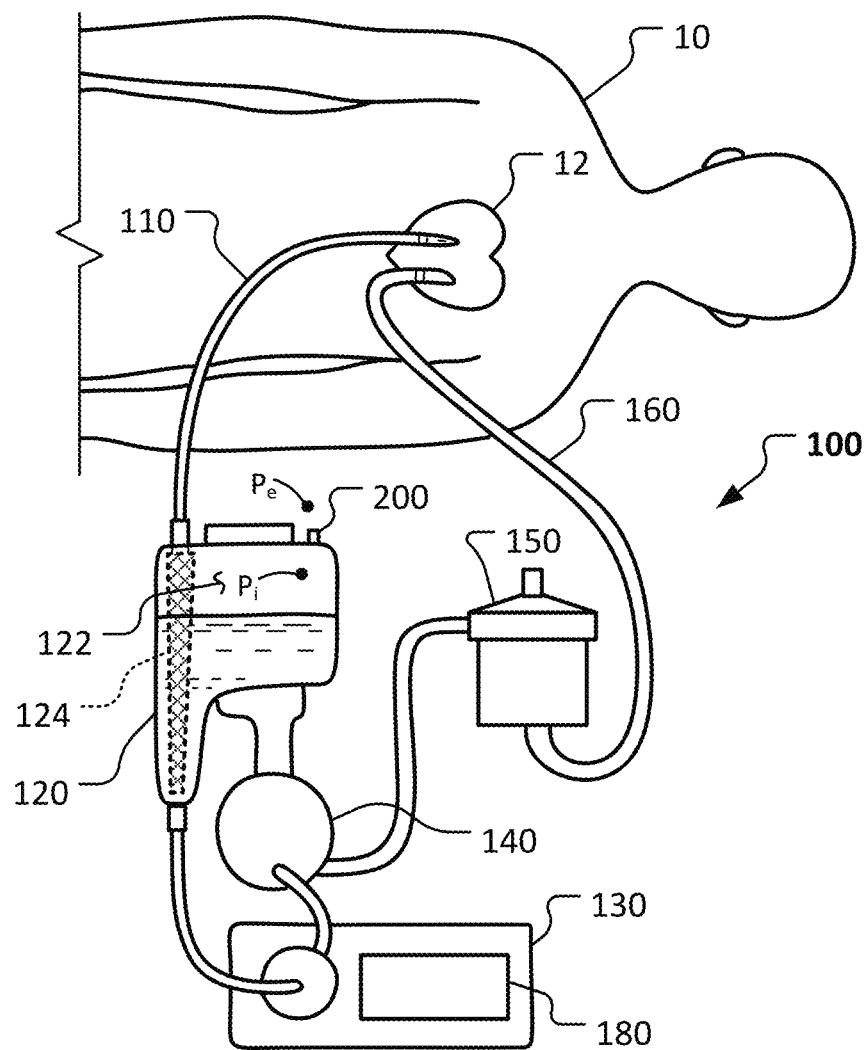
FIG. 1 is a schematic diagram of patient undergoing a medical procedure using a fluid system including a medical fluid reservoir that houses a filter, in accordance with some embodiments provided herein.

This document provides improvements to filters. For example, this document provides filters that have a gradient of filter pore sizes at different portions of the filters. The filters provided herein can be used in medical applications and non-medical applications. For example, this document provides example extracorporeal blood filters that have a gradient of filter pore sizes at different portions of the filter element. As described further below, the gradient of filter pore sizes may enhance the filter's potential for capturing gaseous emboli that may be present in the blood or other fluid that is flowing through the filter.

The devices and methods provided herein are described in the exemplary context of a blood reservoir used for a heart/lung bypass procedure. However, it should be understood that the devices and methods provided herein may be applied in other types of medical fluid systems that include the use of a filter, as well as in non-medical applications.

During a heart/lung bypass surgery, blood flows out of a patient and enters a venous reservoir. A filter is located within the venous reservoir. The purpose of the filter is to remove unwanted materials within the blood, including gaseous bubbles that can become emboli if returned to the patient. As used herein, the term "gaseous emboli" refers to gaseous bubbles whether they reside in a human body or outside the body.

The filter devices in a venous reservoir are typically constructed of a mesh material having a particular average opening size (typically around 40 microns). This size allows blood components to generally freely flow through the filter media while restricting the flow therethrough of at least some of the gaseous emboli. The emboli are trapped from flowing through the filter material, and can either remain trapped in the filter material, get broken up into very tiny emboli that pass through the filter material, or can rise up to the surface of the blood for elimination into an airspace atop the blood surface.

In some implementations, the flow of the blood within the filter housing (e.g., venous reservoir) follows a typical pattern. For example, in some embodiments blood enters the top of the reservoir through a port which is connected to a long tube (sometimes referred to as a drop tube) within the reservoir. In some embodiments, the drop tube is located within a filter surround (e.g., filter sock, cage, housing, or cartridge). This drop tube allows the blood to gently flow down to the bottom of the filter (while still within the reservoir) and to exit from the drop tube with a non-turbulent, non-splashing flow pattern. In this way, the blood is delivered to the bottom of the filter member, typically near the outlet port of the venous reservoir.

Since the blood is delivered close to the outlet port of the reservoir, some of the blood, especially when flowing at higher flow rates, may tend to flow quickly through the filter media and out of the reservoir. This is generally undesirable, as residence time within the filter of the reservoir will allow for gaseous bubbles within the blood to rise up to the blood-air interface in the reservoir, and to thereby be removed from the circulating blood.

Thus, in order to reduce gaseous emboli return to the patient, the gaseous emboli removal efficiency of the venous filter will be improved with increasing residence time of the blood within the filter surround. In some embodiments, this can be accomplished by creating a filter composed of two or more portions of different mesh sizes. A tighter mesh can restrict at least some gaseous bubbles from flowing out of the filter portion, and blood flow through the tighter mesh portion will be reduced, leading to a longer residence time of the blood within the filter. Both of these effects, by virtue of the gradient mesh venous filter, will improve the efficiency of gaseous emboli removal.

The smaller mesh openings at the lower portions of the filter will tend to improve the capture of gaseous emboli, as well as slightly restrict blood flow through the filter, thereby allowing for a longer residence time of blood within the venous reservoir. The larger pore size at higher levels of the filter surround allow for easier blood through-flow, and prevent blood holdup within the venous filter at these levels.

Referring to FIG. 1, a patient 10 can receive a medical treatment while using a medical fluid system 100. In this illustrative example, the patient 10 is undergoing a heart bypass procedure using an extracorporeal blood flow circuit 100. The circuit 100 is connected to the patient 10 at the patient's heart 12 (e.g., the right atrium). Blood from the patient 10 is extracted from the patient 10 at the patient's heart 12; the blood is circulated through the circuit 100; and the blood is then returned to the patient's heart 12 (e.g., at the ascending aorta).

The depicted implementation of the extracorporeal blood flow circuit 100 includes, at least, a venous tube 110 (including a cannula), a blood reservoir 120 (e.g., a housing that includes an internal filter 124), a pump 130, an oxygenator/heat exchanger 140, an arterial filter 150 (optional), an arterial tube 160, and a user interface 180. The venous cannula/tube 110 is in physical contact with the heart 12 and in fluid communication with the venous side of the circulatory system of the patient 10. The venous tube 110 is also in fluid communication with an inlet to the reservoir 120. Blood from the reservoir inlet is directed to flow through the internal filter 124 within the reservoir 120. An outlet from the reservoir 120 is connected by tubing to an inlet of the pump 130. The outlet of the pump 130 is connected to tubing to an inlet of the oxygenator/heat exchanger 140. The outlet of the oxygenator/heat exchanger 140 is connected by tubing to an inlet of the arterial filter 150 (when the arterial filter 150 is included in the circuit 100). An outlet of the arterial filter 150 is connected to the arterial tube 160. The arterial tube 160 is in physical contact with the heart 12 and in fluid communication with the arterial side of the circulatory system of the patient 10. The user interface 180 can include user input and output devices that are used by the clinician operator to properly operate the extracorporeal blood flow circuit 100.

Briefly, the extracorporeal blood flow circuit 100 operates by removing venous blood from the patient 10 via the venous tube 110. Blood from the venous tube 110 is deposited within the internal filter 124 in the reservoir 120. At least some amount of blood is intended to be maintained in the reservoir 120 at all times during the medical procedure. The blood passes through the filter 124 located within the reservoir 120. As described further below, the filter 124 can serve to remove potential emboli, including gaseous bubbles, from the blood. That is, the media of the internal filter 124 has a pore size that prevents through-flow of potential emboli, including gaseous bubbles, that are larger than the pore size.

Blood from the reservoir 120 (after the blood has passed through the filter 124) is drawn from the reservoir 120 by the pump 130. The pump 130 can be operated at various speeds which correspond to various flow rates of blood exiting from the reservoir 120. The pressure generated by the pump 130 propels the blood through the oxygenator/heat exchanger 140. In the oxygenator/heat exchanger 140 the venous blood is enriched with oxygen and adjusted to a desired temperature. The oxygen-rich arterial blood exits the oxygenator/heat exchanger 140, travels through the arterial filter 150 (when the arterial filter 150 is included in the circuit 100), and is injected into the patient's heart 12 by the arterial tube 160.

This document provides improved medical filters that have a gradient of filter pore sizes at different portions of the filter element. As described further below, the gradient of filter pore sizes may enhance the filter's potential for capturing gaseous emboli that may be present in the blood or other fluid that is flowing through the filter such that the gaseous emboli can be eliminated from the circuit 100. Gaseous emboli are typically introduced into the system at the point of cannulation (where the venous tube 110 interfaces with the heart 12). If the opening to the heart 12 (or other portion of the patient's vasculature) is not completely sutured to the cannula 110, then air can be introduced and flow straight to the venous reservoir 120. If this air passes through the entire extracorporeal circuit 100, it will be returned to the patient 10 and delivered into their blood stream. Hence, the filter 124 plays a safety role by eliminating at least some of the gaseous bubbles that may be present in the blood.

The flow of blood through the extracorporeal blood flow circuit 100 is intended to be essentially continuous while the medical procedure is taking place. Within that overall context, an accumulation of blood exists in the reservoir 120 during the procedure. The accumulation of a certain amount of blood in the reservoir 120 is advantageous in some circumstances.

The accumulation of blood within the reservoir 120 serves multiple purposes. For example, in one aspect the accumulation of blood in the reservoir 120 provides a buffer amount to help ensure a continuous flow of oxygenated blood to the patient 10, even in the event that blood flow to the reservoir 120 is interrupted. For example, in some cases a clinician operator of the extracorporeal blood flow circuit 100 may endeavor to maintain an amount of blood in the reservoir that allows for about 12 to 15 seconds of runtime (blood flow to the patient 10) in the event that no more blood is added into the reservoir 120. In another example aspect, the reservoir 120 allows the venous blood to deaerate. The deaeration of the venous blood takes place by allowing air bubbles in the blood to escape the blood and flow upward into an airspace 122 within the reservoir 120. For at least that reason, the airspace 122 is generally maintained in the reservoir 120. It can be envisioned from the forgoing description, that when the blood incurs a longer dwell time within the reservoir 120, more opportunity to deaerate the blood is advantageously attained.

While this description of the filters with gradient pore sizes is illustrated in the context of an example blood reservoir used in an extracorporeal circuit, it should be understood that the inventive concepts provided herein are not limited to such an implementation. For example, the filters with gradient pore sizes can be incorporated into filters within general filter canisters or housings and the like. Accordingly, in some embodiments the filters with gradient pore sizes are incorporated into devices such as, but not limited to, the arterial filter 150.

Figure 2:
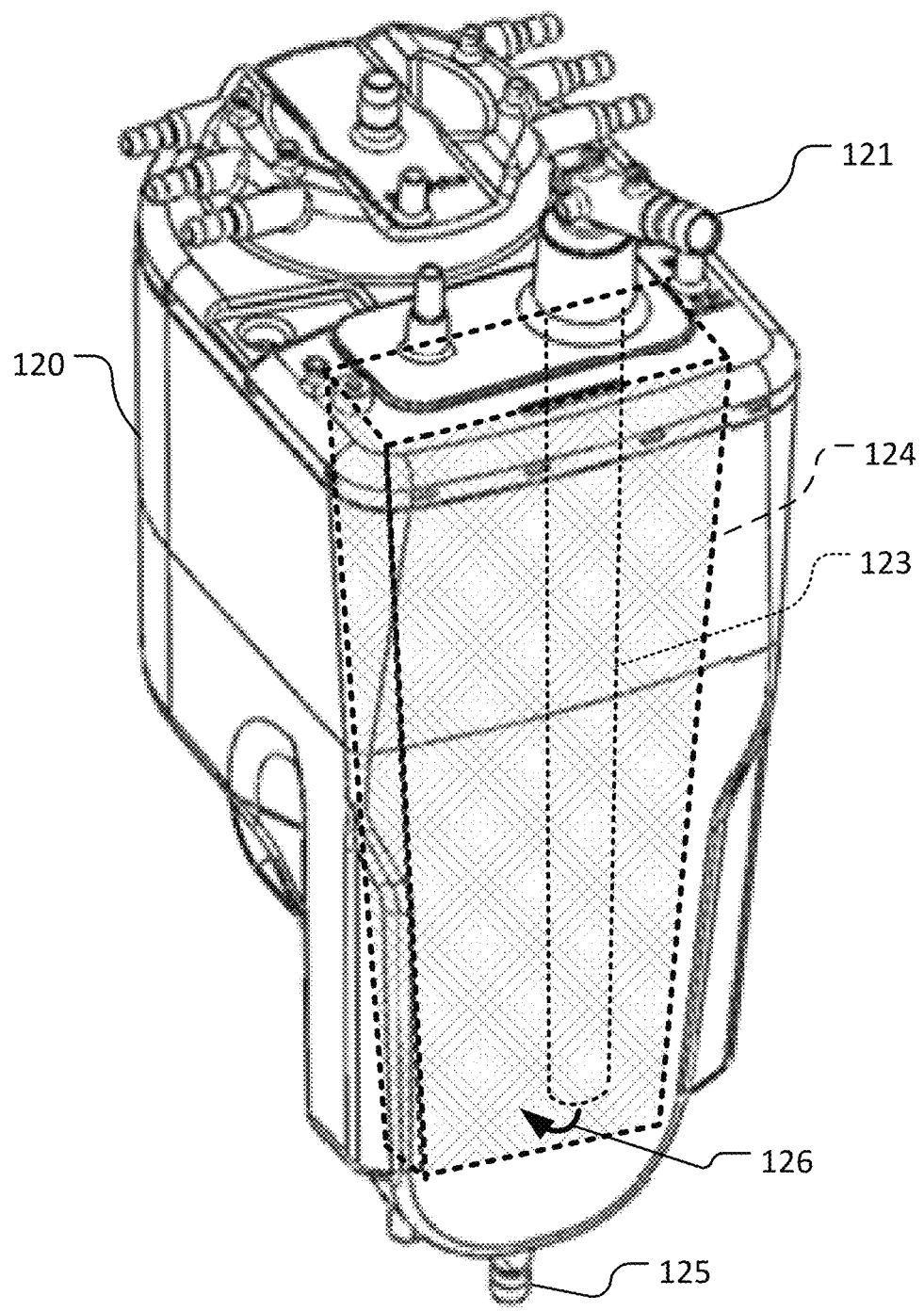
FIG. 2 is a perspective view of an example filter mounted in a medical fluid reservoir, in accordance with some embodiments provided herein.

With reference also to FIG. 2, the reservoir 120 can include the filter 124 within the interior space defined by the reservoir 120. As described further below, in some embodiments the filter 124 is comprised of a mesh material with gradient pore sizes as provided herein. In some implementations, the filter 124 is referred to as the venous blood filter, and the reservoir 120 also includes one or more other types of filters such as a cardiotomy filter.

In the depicted embodiment, the filter 124 is configured in a filter sock or bag configuration. That is, the lower end (also referred to herein as the second end) of the filter 124 is closed (like the toe portion of a sock or the bottom of a bag). In some embodiments, the upper end (also referred to herein as the first end) of the filter 124 is open. Alternatively, in some embodiments the upper end of the filter 124 is also closed (like the lower end). In some embodiments, a structural framework is coupled with the filter 124 to enhance the structural rigidity of the filter 124. In some such embodiments, the structural framework is coupled inside the filter 124. In some such embodiments, the structural framework is coupled outside the filter 124. In some such embodiments, the structural framework is coupled inside and outside the filter 124.

While in the depicted embodiment the filter 124 is configured in a filter sock configuration, in some embodiments the filter 124 is configured as a sheet, a cartridge, a pleated configuration, a planar configuration, and other types of filter configurations, and combinations thereof. In some embodiments, the filter 124 is combined with one or more other types of filtering materials and/or other elements that direct or divert the flow of the material being filtered.

The reservoir 120 also includes a blood inlet 121, a drop tube 123, and a blood outlet 125. The blood inlet 121 (located at an upper portion of the housing of reservoir 120), receives inflowing blood from venous tube 110. A first end of the drop tube 123 is coupled with the blood inlet 121. A second end of the drop tube 123 is located near the lower end (second end) of the filter 124.

Blood flowing into the reservoir 120 travels along a path as follows. The blood flows into the blood inlet 121 and then into the first end of the drop tube 123. The blood flows through the drop tube 123, and exits the drop tube 123 at the second end of the drop tube 123 as depicted by arrow 126. The blood exiting from the drop tube 123 flows into an interior space (or chamber) defined by the filter 124 and the upper airspace 122 (refer to FIGS. 1 and 2). The blood needs to pass through the wall of the filter 124 in order to exit the reservoir 120 via the blood outlet 125 (located at a lower portion of the housing of reservoir 120).

Because of where the blood enters the filter 124 and the shape of the filter 124, blood flowing into the filter 124 initially contacts the filter 124 at or near the second end (lower end) thereof The filter 124 will tend to restrict the flow of the blood through the filter 124. The smaller the pore size of the filter 124 at the second end, the more the filter 124 will restrict the flow of blood through the filter 124. Consequently, the blood will tend to spend time (dwell) within the interior of the filter 124 at or near the second end. As blood dwells within the interior of the filter 124 at or near the second end, at least some of the gaseous bubbles in the blood will be allowed to rise to the top surface of the blood, and to escape the blood by entering into the airspace 122. The longer the dwell time of the blood in the filter 124 the greater the opportunity for entrained gases (e.g., air) to exit the blood by rising to the top surface of the blood and be released into the airspace 122. Further, the longer the dwell time of the blood in the filter 124 the more the height of the blood in the filter 124 rises. It also follows that the more restrictive the filter 124 is (i.e., the smaller the pore size), the longer the blood will tend to dwell in the interior of the filter 124. Hence, it can be said that by making the pore size of the filter 124 more restrictive (finer), the potential for removing gaseous bubbles is enhanced.

Additionally, by making the pore size of the filter 124 more restrictive, more potential embolic material will be captured by filter 124. Hence, by making the pore size of the filter 124 more restrictive, rather than allowing a particular size of bubble through the filter 124, the filter 124 will tend to block small bubbles that otherwise might pass through the filter 124.

While making the pore size of the filter 124 more restrictive can provide the aforementioned benefits, one of skill in the art will recognize that a potentially undesired result of making the filter 124 more restrictive is that the rate of blood flow through the filter 124 and through the reservoir 120 as a whole may be reduced. In some cases, the reduced blood flow rate may not even be sufficient to support the needs of the extracorporeal blood flow circuit 100 and the patient. Hence, the need for a balance between a restrictive and a free-flowing filter media for filter 124 is recognized.

With reference to FIG. 3, an example filter 300 can include a gradient of pore sizes at different portions of the filter 300. The example filter 300 includes a first filter portion 310, a second filter portion 320, a third filter portion 330, and a fourth filter portion 340. The first filter portion 310 is located at the second end portion 304 (lower end portion, relative to vertical) of the filter 300. The second filter portion 320 is disposed adjacent to the first filter portion 310. The third filter portion 330 disposed adjacent to the second filter portion 320. The fourth filter portion 340 is disposed adjacent to the third filter portion 330 and is located at the first end portion 302 (upper end portion, relative to vertical) of the filter 300.

The filter portions 310, 320, 330, and 340 can be combined together by various methods to become an essentially one-piece filter 300. For example, in some embodiments the filter portions 310, 320, 330, and 340 are attached together by welding or gluing them to each other. In some embodiments, the filter portions 310, 320, 330, and 340 are sewn, woven, knitted, clipped, melted, clamped, welded, or otherwise attached together. In some embodiments, the filter portions 310, 320, 330, and 340 are individually attached to a framework.

The filter portions 310, 320, 330, and 340 can be made of any type of suitable filter material. In some embodiments, the filter portions 310, 320, 330, and 340 are made of a polyethylene, polyurethane, nylon, ePTFE, or another type of synthetic material. In some embodiments, the filter portions 310, 320, 330, and 340 are made of cotton, carbon, or another type of natural material. In some embodiments, the filter portions 310, 320, 330, and 340 are made of a combination of materials. In some embodiments, one or more of the filter portions 310, 320, 330, and 340 is made of a material that is different than the material of one or more of the other filter portions 310, 320, 330, and 340.

Example filter 300 is configured with four portions that have differing relative pore sizes. It should be understood that, in some embodiments, two, three, five, six, seven, eight, nine, ten, or more than ten portions that have differing relative pore sizes can be included in a single filter embodiment.

In the depicted embodiment, the first filter portion 310 has a smaller pore size than each of the other filter portions of the filter 300. The second filter portion 320 has the next smallest pore size (i.e., its pore size is larger or coarser than that of the first filter portion 310). The third filter portion 330 has a pore size that is larger (coarser) than both the first filter portion 310 and the second filter portion 320. The fourth filter portion 340 has the largest (coarsest) pore size of all. That is, the fourth filter portion 340 has a pore size that is larger than each of the first filter portion 310, the second filter portion 320, and the third filter portion 330.

It should be understood that the aforementioned arrangement of relative filter pore sizes is merely exemplary. That is, the inventive concepts provided in this disclosure are not limited to the aforementioned arrangement of filter portions with their relative pore sizes. For example, in some embodiments a middle portion may have the smallest relative pore size, or an upper portion may have the smallest relative pore size.

In some embodiments, the first filter portion 310 has an average pore size of about 20 microns. In some embodiments, the second filter portion 320 has an average pore size of about 30 microns. In some embodiments, the third filter portion 330 has an average pore size of about 40 microns. In some embodiments, the fourth filter portion 340 has an average pore size of about 50 microns. It should be understood that the preceding pore sizes are merely exemplary. That is, the pore sizes of the filter portions 310, 320, 330, and 340 can be of any average size. In some embodiments, the uppermost filter portion may have a very large pore size (relatively speaking in comparison to the other filter portions) to provide an emergency release of blood from within the interior of the filter 300 so as to prevent over pressurization and/or lack of flow through the filter 300.

While the lower end portion(s) of the filter 300 have small pore sizes that restrict gaseous bubbles above a certain size from flowing therethrough, the upper end portion(s) of the filter 300 have larger pore sizes that could allow at least some of such gaseous bubbles to flow therethrough. However, at least in some scenarios the buoyancy of the gaseous bubbles is not overcome by the forces from the current(s) of the blood flowing through the upper end portion(s) of the filter 300. Hence, even though the gaseous bubbles could (from a size perspective) flow through the upper end portion(s) of the filter 300, the gaseous bubbles will tend to not do so, and will flow into the upper air space 122 (refer to FIG. 1) instead.

With reference to FIG. 4, another example filter 400 can include a gradient of pore sizes at different portions of the filter 400. While the example filter 300 described above includes distinct or discrete filter portions that have differing average pore sizes, the example filter 400 is made of a single-piece of filter material 410 (a continuous piece) that has a gradually changing pore size along the length of the filter 400. The filter 400 can be made of any of the materials described above in reference to the filter 300.

Filter 400 includes a first end portion 402 and a second end portion 404. In some embodiments, the first end portion 402 is positioned as the upper end portion (relative to vertical) and the second end portion 404 is positioned as the lower end portion (e.g., refer to FIGS. 1 and 2 where airspace 122 is located at the upper end).

In the depicted embodiment, the filter material 410 has its smallest (finest) pore size at the second end portion 404 and its largest (coarsest) pore size at the first end portion 402. The average pore size of the filter material 410 reduces in size from the first end portion 402 to the second end portion 404. In some embodiments, the average pore size of the filter material 410 reduces in size from the first end portion 402 to the second end portion 404 according to an essentially linear function. In some embodiments, the average pore size of the filter material 410 reduces in size from the first end portion 402 to the second end portion 404 according to step function, or a combination of linear and step functions. In some embodiments, the average pore size of the filter material 410 reduces in size from the first end portion 402 to the second end portion 404 according to another mathematical function.

While in the depicted embodiment the filter material 410 has its smallest pore size at the second end portion 404 and its largest pore size at the first end portion 402, such an arrangement is not required in all embodiments. For example, in some embodiments a middle portion of the filter material 410 may have the largest relative pore size of the filter material 410. It should be understood that any and all potential distributions of pore size of the filter material 410 are within the scope of this disclosure.

While the lower end portion(s) of the filter 400 have small pore sizes that restrict gaseous bubbles above a certain size from flowing therethrough, the upper end portion(s) of the filter 400 have larger pore sizes that could allow at least some of such gaseous bubbles to flow therethrough. However, at least in some scenarios the buoyancy of the gaseous bubbles is not overcome by the forces from the current(s) of the blood flowing through the upper end portion(s) of the filter 400. Hence, even though the gaseous bubbles could (from a size perspective) flow through the upper end portion(s) of the filter 400, the gaseous bubbles will tend to not do so, and will flow into the upper air space 122 (refer to FIG. 1) instead.

In some embodiments, the filter materials and/or types of construction of filters 300 and 400 can be combined to create a hybrid filter design which is also within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A venous blood reservoir for use in an extracorporeal circuit, the reservoir comprising:
    an outer housing defining an internal space, the outer housing having an upper housing portion and a lower housing portion; and
    a venous filter comprising a porous filter material disposed within the internal space, the filter having an upper filter end portion and a lower filter end portion, the upper filter end portion disposed adjacent the upper housing portion and the lower filter end portion disposed adjacent the lower housing portion,
        wherein an average pore size of the porous filter material disposed at the lower filter end portion is less than an average pore size of the porous filter material disposed at the upper filter end portion.

2. The reservoir of claim 1, wherein the venous filter comprises three or more distinct portions of the porous filter material.

3. The reservoir of claim 1, the venous filter also having a middle filter portion disposed between the upper filter end portion and the lower filter end portion, wherein an average pore size of the porous filter material disposed at the middle filter portion is larger than the average pore size of the porous filter material disposed at the lower filter end portion, and wherein the average pore size of the porous filter material disposed at the middle filter portion is less than the average pore size of the porous filter material disposed at the upper filter end portion.

4. The reservoir of claim 1, further comprising a cardiotomy filter.

5. The reservoir of claim 1, wherein the venous filter comprises a continuous piece of the porous filter material that has a gradually changing pore size along a length of the filter.

6. The reservoir of claim 1, wherein the venous filter comprises four or more distinct portions of the porous filter material.

7. The reservoir of claim 1, wherein the average pore size of the porous filter material disposed at the lower filter end portion is less than 40 microns, and wherein the average pore size of the porous filter material disposed at the upper filter end portion is greater than 40 microns.

8. A method of using an extracorporeal circuit during a surgery on a patient, the method comprising:
    transferring blood from the patient into a venous blood reservoir, the venous blood reservoir comprising:
        an outer housing defining an internal space, the outer housing having an upper housing portion and a lower housing portion; and
        a venous filter comprising a porous filter material disposed within the internal space, the filter having an upper filter end portion and a lower filter end portion, the upper filter end portion disposed adjacent the upper housing portion and the lower filter end portion disposed adjacent the lower housing portion,
            wherein an average pore size of the porous filter material disposed at the lower filter end portion is less than an average pore size of the porous filter material disposed at the upper filter end portion;
    passing the blood through the venous filter, wherein the average pore size of the porous filter material disposed at the lower filter end portion adapts the venous filter to cause the blood to dwell within the venous filter for a longer period of time than the blood would dwell if the pore size of the lower filter end portion was the same as the pore size of the upper filter end portion, thereby allowing for improved removal of gaseous emboli from the blood; and
    draining the blood out of the venous blood reservoir.

9. The method of claim 8, wherein the average pore size of the porous filter material disposed at the lower filter end portion is less than 40 microns, and wherein the average pore size of the porous filter material disposed at the upper filter end portion is greater than 40 microns.

10. The method of claim 8, wherein at least some gaseous bubbles are removed from the blood by the venous filter as the blood passes through the filter.

11. The method of claim 8, wherein at least some gaseous bubbles are broken into smaller gaseous bubbles by the venous filter as the blood passes through the filter.

12. A medical filter comprising:
    a housing defining an internal space and a longitudinal axis, the housing having an upper housing portion and a lower housing portion; and
    a filter element comprising a porous filter material disposed in general longitudinal alignment within the internal space, the filter element having an upper portion and a lower portion,
        wherein the porous filter material disposed at the lower portion is finer than the porous filter material disposed at the upper portion.

13. The medical filter of claim 12, wherein the filter element comprises three or more distinct portions of the porous filter material.

14. The medical filter of claim 12, the filter element also having a middle portion disposed between the upper portion and the lower portion, wherein the porous filter material disposed at the middle portion is coarser than the porous filter material disposed at the lower portion, and wherein the porous filter material disposed at the middle portion is finer than the porous filter material disposed at the upper portion.

15. The medical filter of claim 12, wherein the filter element comprises two or more distinct portions of the porous filter material.

16. The medical filter of claim 12, wherein the filter element comprises a continuous piece of the porous filter material that has a gradually changing pore size along a length of the filter element.

17. The medical filter of claim 12, wherein the filter element comprises four or more distinct portions of the porous filter material.

18. A method of filtering blood through a filtering system, the method comprising:
  inputting the blood to the filtering system at a bottom region of a chamber defined by a filter and an upper air space, the filter comprising a porous filter material, the filter having an upper end portion and a lower end portion, wherein an average pore size of the porous filter material disposed at the lower end portion is less than an average pore size of the porous filter material disposed at the upper end portion; and
  filtering the blood such that the blood flows outwardly through pores in the filter while gaseous bubbles prevented from flowing through the pores in the filter rise in the chamber toward the upper air space.

19. The method of claim 18, wherein the average pore size of the porous filter material disposed at the lower end portion is less than 40 microns, and wherein the average pore size of the porous filter material disposed at the upper end portion is greater than 40 microns.

* * * * *

UNITED STATES PATENT AND TRADEMARK OFFICE
CERTIFICATE OF CORRECTION

PATENT NO. : 9,827,364 B2
APPLICATION NO. : 14/728241
DATED : November 28, 2017
INVENTOR(S) : Louis F. Peticca, Jeffrey E. Troyan and Eric E. Brooking It is certified that error appears in the above-identified patent and that said Letters Patent is hereby corrected as shown below:

On the Title Page

Item (71), delete "Terumo Cardiovascular Systems, Inc." and insert --Terumo Cardiovascular Systems Corporation--;

Item (73), delete "Terumo Cardiovascular Systems, Inc." and insert --Terumo Cardiovascular Systems Corporation--.

Signed and Sealed this
Twenty-fourth Day of April, 2018

Andrei Iancu
*Director of the United States Patent and Trademark Office*